(12) United States Patent
Ricci (10) Patent No.: US 10,460,839 B1
(45) Date of Patent: Oct. 29, 2019

(54) DATA MINING OF DENTAL IMAGES

(71) Applicant: Richard Ricci, New York, NY (US)

(72) Inventor: Richard Ricci, New York, NY (US)

(*) Notice: Subject to any disclaimer, the term of this patent is extended or adjusted under 35 U.S.C. 154(b) by 0 days.

(21) Appl. No.: 16/203,795

(22) Filed: Nov. 29, 2018

(51) Int. Cl.
*G16H 30/40* (2018.01)
*G06T 7/00* (2017.01)
*G16H 30/20* (2018.01)

(52) U.S. Cl.
CPC .......... *G16H 30/40* (2018.01); *G06T 7/0012* (2013.01); *G06T 2207/20081* (2013.01); *G16H 30/20* (2018.01)

(58) Field of Classification Search
CPC ........ G16H 50/20; G16H 10/60; G16H 40/20; G16H 40/63; G16H 50/30; G16H 20/30; G16H 40/67; G16H 50/50; G16H 50/70; G16H 10/40; G16H 20/17; G16H 30/20; G16H 40/60; G16H 20/04; A61C 7/002; A61C 7/08; G06F 19/321; A61Q 11/00; G06Q 10/10; G06Q 50/22
See application file for complete search history.

(56) References Cited

U.S. PATENT DOCUMENTS

| | | |
|---|---|---|
| 7,930,189 B2 | 4/2011 | Kuo |
| 8,095,383 B2 | 1/2012 | Arnone et al. |
| 8,099,305 B2 | 1/2012 | Kuo et al. |
| 2002/0178032 A1 | 11/2002 | Benn et al. |
| 2003/0050803 A1* | 3/2003 | Marchosky ............ G16H 10/60 705/3 |
| 2005/0108052 A1 | 5/2005 | Omaboe |
| 2005/0192835 A1 | 9/2005 | Kuo et al. |
| 2007/0106537 A1 | 5/2007 | Moore |
| 2007/0168152 A1 | 7/2007 | Matov et al. |
| 2008/0085487 A1* | 4/2008 | Kuo ...................... G06Q 50/22 433/24 |
| 2008/0208914 A1 | 8/2008 | Navani |
| 2014/0188510 A1* | 7/2014 | Samari .................. G16H 10/60 705/3 |
| 2016/0379173 A1 | 12/2016 | Karnati et al. |
| 2018/0078347 A1* | 3/2018 | Falkel .................. A61C 9/0046 |

FOREIGN PATENT DOCUMENTS

KR 101639789 B1 3/2018

* cited by examiner

*Primary Examiner* — Joseph D Burgess
(74) *Attorney, Agent, or Firm* — Gearhart Law LLC (57) ABSTRACT

Data mining of a dental image is described. In an example scenario, an aggregator service receives a dental image of a patient from a dental image provider. The dental image is processed with a machine learning (ML) anatomy dataset. An anatomy from the ML anatomy dataset is identified and matched to the dental image. The dental image is next matched and identified with a ML pathology and treatment dataset. A pathology and a treatment from the ML pathology and treatment dataset are matched to the dental image. Next, the dental image and the anatomy, the pathology, and the treatment associated with the dental image are inserted to a patient dataset associated with the patient. A cluster analysis of the patient dataset is performed with a cluster dataset to produce a correlated dental image information. The correlated dental image information is provided to a data mining entity and to compile a diagnostic aid for a user.

17 Claims, 6 Drawing Sheets

DATA MINING OF DENTAL IMAGES

CLAIM OF PRIORITY

This application is a United States non-provisional application and claims no priority to any previous United States patent application.

FIELD OF THE EMBODIMENTS

The field of the embodiments relate to a system to provide data mining of a dental image. The dental image (received from a source such as an x-ray capture device) may be processed by a machine learning mechanism to analyze the dental image.

BACKGROUND OF THE EMBODIMENTS

Information exchange have changed processes associated work and personal environments. Automation and improvements in processes have expanded scope of capabilities offered for personal and business data consumption. With the development of faster and smaller electronics, execution of mass processes at cloud systems have become feasible. Indeed, applications provided by data centers, data warehouses, data workstations have become common features in modern personal and work environments. Patient data management service(s) provide a wide variety of applications ranging from hosting, management, and/or presentation of patient information.

Below are some examples of patient data management systems.

U.S. Pub. 2005/0108052 pertains to a medical (human and veterinary) CRM and ERP software that affects every step of patient interaction: marketing, sales or service-related. It allows management of the workload by distributing the chores among staff members and automates medical and business processes through workflow rules. It enables users to view and update tasks, medical cases, appointments, sales, phone calls, faxes, emails, letters and automatic input of lab results into the patient's medical record U.S. Pub. 2002/0178032 pertains to a method and system is provided for charting tooth decay to assist in caries management. Specifically, the invention provides a computer system, a Graphical User Interface (GUI), a method, and associated computer code for presenting an interactive tooth chart comprising selectable, anatomically correct tooth icons corresponding to a dental patient's teeth. The invention allows a user to select regions of each individual tooth icon to record the condition of the selected region. According to the invention, a dental patient is selected from a patient data base, the patent's teeth are examined, and the condition of each tooth region is recorded using selectable icons.

U.S. Pat. No. 7,030,189 pertains to a method and system for providing dynamically generated orthodontic profile and associated treatment information.

U.S. Pub. 2008/020891 pertains to a remote logical interface for mining medical data records comprises a data processor for receiving input of a selection of criteria for a medical records query, a database of medical records, responsive to a query, for outputting patient medical record data responsive to the query, and a plurality of operations including a means of combining a first and second query and a means of providing medical data not meeting the first and second query.

Korean Pat. KR101839784 pertains to a data generating system for reading a dental image.

None of the art described above addresses all of the issues that the present invention does.

SUMMARY OF THE EMBODIMENTS

The present invention and its embodiments relate to data mining of a dental image. A system may provide data mining of the dental image. The system may include an aggregator server. The aggregator server may be configured to receive a dental image of a patient from a dental image provider. An example of the dental image provider may include a patient, a dentist, a doctor, an insurance company, an e-commerce service, and/or a cloud based storage service, among others. Next, the dental image may be processed with a machine learning (ML) anatomy dataset. An anatomy from the ML anatomy dataset may be identified and matched to the dental image. The dental image may also be matched and identified with a ML pathology and treatment dataset. A pathology and a treatment from the ML pathology and treatment dataset may be matched to the dental image. Subsequently, the dental image and the anatomy, the pathology, and the treatment associated with the dental image may be inserted to a patient dataset associated with the patient. In addition, a cluster analysis of the patient dataset may be performed with a cluster dataset to produce a correlated dental image information. Furthermore, the correlated dental image information may be provided to a data mining entity and to compile a diagnostic aid for a user.

In another embodiment of the present invention, an aggregator server for providing data mining of a dental image is described. The aggregator server may include a computer vision component configured to analyze the dental image, a memory configured to store instructions associated with an aggregator service, and a processor coupled to the computer vision component and the memory. The processor may execute the instructions associated with the aggregator service. The aggregator service may include an image processing engine. The image processing engine may be configured to receive a dental image of a patient from a dental image provider. An example of the dental image provider may include a patient, a dentist, a doctor, an insurance company, an e-commerce service, and/or a cloud based storage service, among others. The dental image may next be processed with a ML anatomy dataset. An anatomy from the ML anatomy dataset may be identified and matched to the dental image. The dental image may also be matched and identified with a ML pathology and treatment dataset. A pathology and a treatment from the machine leaning pathology and treatment dataset may be matched to the dental image. In addition, a patient dataset of the patient associated with the dental image may be queried and received from a patient data provider. Subsequently, the dental image and the anatomy, the pathology, and the treatment associated with the dental image may be inserted to the patient dataset. Furthermore, a cluster analysis of the patient dataset may be performed with a cluster dataset to produce a correlated dental image information. Moreover, the correlated dental image information may be provided to a data mining entity and to compile a diagnostic aid for a user.

In yet another embodiment of the present invention, a method of providing data mining of a dental image is described. The method may include receiving a dental image of a patient from a dental image provider. An example of the dental image provider may include a patient, a dentist, a doctor, an insurance company, an e-commerce service, and/ or a cloud based storage service, among others. The dental image may next be processed with a ML anatomy dataset. An anatomy from the ML anatomy dataset may be identified and matched to the dental image. The dental image may also be matched and identified with a ML pathology and treatment dataset. A pathology and a treatment from the machine leaning pathology and treatment dataset may be matched to the dental image. In addition, a patient dataset of the patient associated with the dental image may be queried and received from a patient data provider. Subsequently, the dental image and the anatomy, the pathology, and the treatment associated with the dental image may be inserted to the patient dataset. Furthermore, a cluster analysis of the patient dataset may be performed with a cluster dataset to produce a correlated dental image information. Moreover, the correlated dental image information may be provided to a data mining entity and to compile a diagnostic aid for a user.

It is an object of the embodiments of the present invention to provide data mining of a dental image.

It is an object of the embodiments of the present invention to determine an anatomy, a pathology, and a treatment associated with the dental image.

It is an object of the embodiments of the present invention to produce a correlated dental image information associated with a patient dataset and a cluster dataset.

It is an object of the embodiments of the present invention to provide the correlated dental image information to a data mining entity to compile a diagnostic aid for a user.

These and other features, aspects and advantages of the present invention will become better understood with reference to the following drawings, description and claims.

DESCRIPTION OF THE PREFERRED
EMBODIMENTS

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations may be made thereto.

Figure 1:
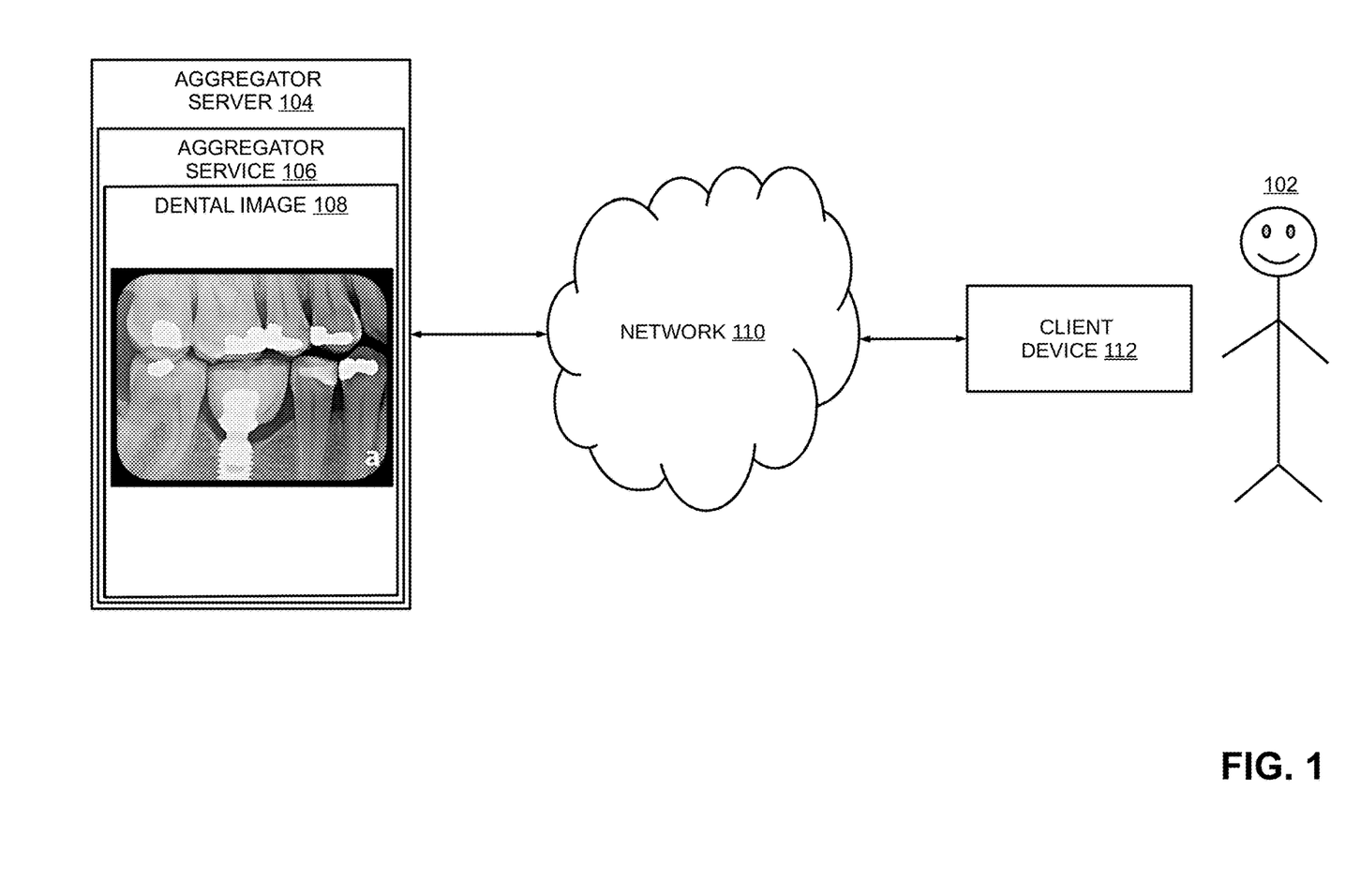
FIG. 1 shows a conceptual diagram illustrating examples of providing data mining of a dental image, according to an embodiment of the invention.

FIG. 1 shows a conceptual diagram illustrating examples of providing data mining of a dental image. In an example scenario, an aggregator server 104 may execute (or provide) an aggregator service 106. The aggregator server 104 may include a physical server providing service(s), application(s), and/or an interface to client devices. A service (such as the aggregator service 106) may include an application performing operations in relation to a client application and/or a subscriber, among others. The aggregator server 104 may include and/or is part of a workstation, a data warehouse, a data center, and/or a cloud based distributed computing source, among others.

In an example scenario, the aggregator server 104 may execute the aggregator service 106. The aggregator service 106 may receive a dental image 108 of a patient from a dental image provider. The dental image 108 may be obtained from a film based x-ray, a digitally scanned x-ray, a digitally captured x-ray, a scintillator technology based image, a trans-illumination image, a florescence technology based image, a blue florescence technology based image, a laser based technology based image, a computed tomography (CT) scan based image of a section and/or an entirety of a mouth of the patient, and/or all future embodiments.

The dental image provider may utilize an image capture device and/or a storage device. The image capture device may include an x-ray equipment, a scintillator counter, an indirect or direct flat panel detector (FPD), a charged couple device (CCD), a phosphor plate radiography device, a picture archiving and communication system (PACS), a photo-stimulable phosphor (PSP) device, a computer tomography (CT) device, a wireless complementary metal-oxide-semiconductor (CMOS), a cone beam computed tomography (CBCT) device, and/or all future embodiments.

Next, the dental image 108 may be processed with a machine learning (ML) anatomy dataset. The ML anatomy dataset may include a number of dental images with annotations associated with anatomical structures. An anatomy from the ML anatomy dataset may be identified and matched to the dental image 108. Furthermore, the dental image may also be matched and identified with a ML pathology and treatment dataset. The ML pathology and treatment dataset may include pathology and treatment annotations associated with a number dental images. A pathology and a treatment from the ML pathology and treatment dataset may be matched to the dental image 108.

Subsequently, the dental image 108 and the anatomy, the pathology, and the treatment associated with the dental image 108 may be inserted to a patient dataset associated with the patient. The patient dataset may include attributes and other information associated with the patient. In addition, a cluster analysis of the patient dataset may be performed with a cluster dataset to produce a correlated dental image information. The cluster dataset may include annotated information associated with a population and dental classifications associated with the population. Furthermore, the correlated dental image information may be provided to a data mining entity to compile a diagnostic aid for a user 102. The data mining entity may include a bioinformatics service associated with a bioinformatics organization and/or a dental (and/or medical) insurance service associated with a dental (and/or medical) insurance organization. The user 102 may include a dentist, a doctor, a patient, a law enforcement entity, a research entity, and/or a data mining entity, among others.

The dental image 108 and the patient dataset (annotated with the anatomy, the pathology and the treatment) and/or the correlated dental image information may be provided to the user 102 through a client device 112. An example of the client device 112 may include a dental office server, a network node, a desktop computer, a workstation, a laptop computer, a tablet, a cellular phone, and/or a mobile device, among others. The user 102 may also include a dentist, a dental technician, a hygienist, a patient, a representative of the patient, and/or a data mining entity among others. The user 102 may be provided with the patient dataset and/or the correlated dental image information as the diagnostic aid in exchange for an integration of the dental image 108 and/or annotation(s)/information associated with the dental image 108 into the cluster dataset, the ML anatomy dataset, the ML pathology and treatment dataset, and/or dataset(s) associated with data mining entity(s), among others.

The aggregator server 104 may communicate with the client device 112 through a network 110. The network 110 may provide wired or wireless communications between network nodes such as the client device 112, and/or the aggregator server 104, among others. Previous example(s) to provide data mining of the dental image 108 are not provided in a limiting sense. Alternatively, the aggregator service 106 may receive the dental image 108, process the dental image 108, and provide the (annotated) patient dataset and the correlated dental image information as a desktop application, a workstation application, and/or a server application, among others. Client application(s) executed by the client device 112 may also include client interface(s) of (or interacting with) the aggregator service 106.

The user 102 may also interact with the client application(s) on the client device 112 with a keyboard based input, a mouse based input, a voice based input, a pen based input, and a gesture based input, among others. The gesture based input may include one or more touch based actions such as a touch action, a swipe action, and a combination of each, among others.

While the example system in FIG. 1 has been described with specific components including the aggregator server 104, the aggregator service 106, embodiments are not limited to these components or system configurations and can be implemented with other system configuration employing fewer or additional components.

Figure 2:
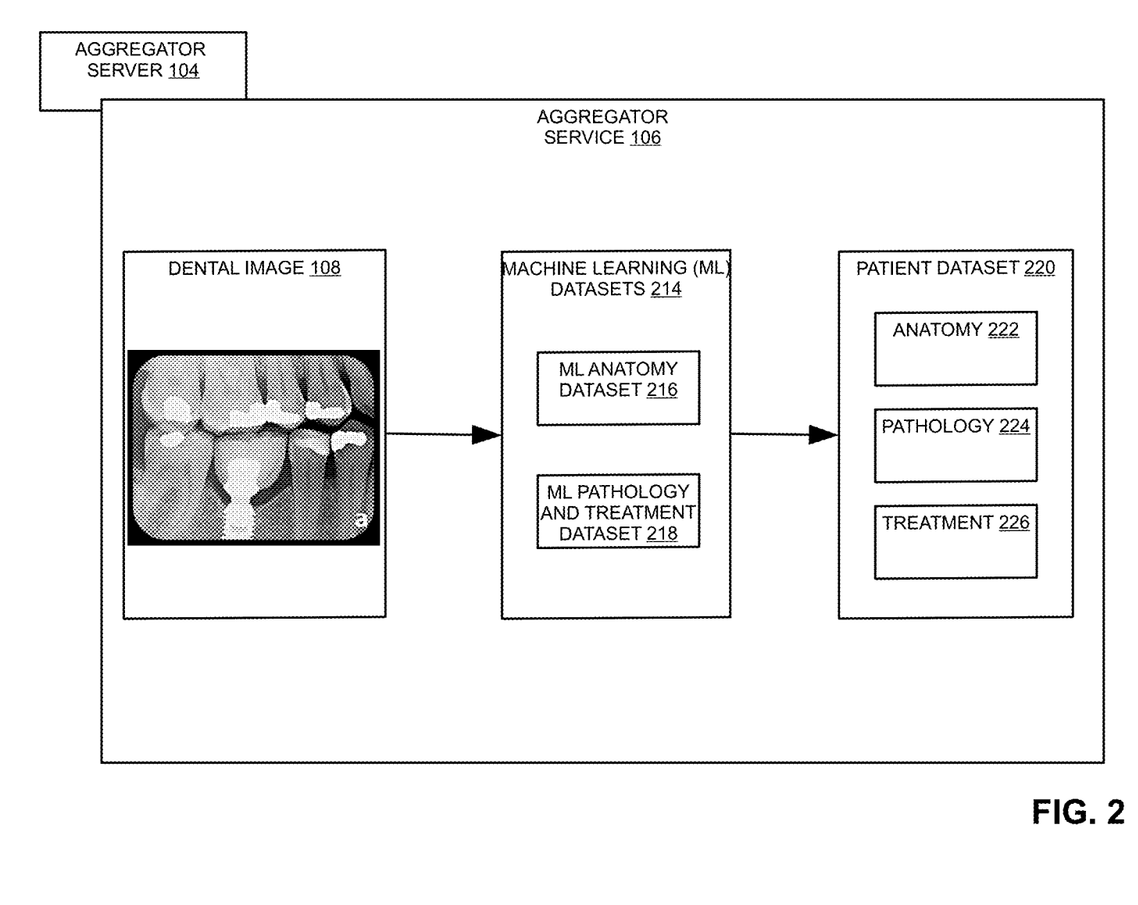
FIG. 2 shows a display diagram illustrating a machine learning mechanism to provide data mining of a dental image, according to an embodiment of the invention.

FIG. 2 shows a display diagram illustrating a ML mechanism to provide data mining of a dental image. The aggregator server 104 may execute the aggregator service 106 that processes the dental image 108 with ML datasets 214.

In an example scenario, the aggregator service 106 may process the dental image 108 with a ML anatomy dataset 216. An anatomy 222 from the ML anatomy dataset 216 may be identified and matched to the dental image 108. The anatomy 222 may be determined by performing ML operation(s). The ML operation(s) may include differentiating the dental image 108 as a left or a right vertical bite wing image; differentiating the dental image 108 as a left or a right horizontal bite wing image; differentiating the dental image 108 as a left or a right maxillary periapical image; differentiating the dental image 108 as a left or a right mandibular periapical image; differentiating the dental image 108 as a maxillary or mandibular anterior image; differentiating the dental image 108 as a left or a right side of a panoramic image, differentiating the dental image 108 as including an absent tooth or a present tooth; and differentiating the dental image 108 as including a cephalometric image with an over bite, an over jet, an angle's classification of malocclusion, an airway space or a sleep apnea.

The anatomy 222 may also be determined by performing additional ML operation(s). The additional ML operation(s) may include differentiating the dental image 108 as a maxillary image or a mandible image; differentiating the dental image 108 as a left or a right temporal mandibular joint image; identifying and measuring a mandibular canal, an inferior alveolar nerve space, a mental foramen, a staphne's cyst, a mandible foramen, a condylar process, a mandibular coronoid process, a sublingual fossa, a ramus, a alveolar crest, a mental protuberance, a mental tubercle, a mylohyoid grove, a mylohyoid line, a lingual, a pterygoid fossa, an incisive canal, a zygomatic bone, a maxillary sinus, a curve of spee, a diastomer, a tooth bud, a germination, a fused teeth, a full or partial septum, an open bite, a cross bite, an over jet, and/or an over bite associated with the dental image 108; identifying and measuring a maxillary sinus size and volume, a bone thickness of a floor of a maxillary sinus, a bone thickness surrounding the maxillary sinus, a graft placed in the maxillary sinus, and/or a septum in the maxillary sinus; identifying a post-surgical maxillary sinus or mandibular alveolar ridge splitting procedure; and identifying a frontal sinus, a graft placed in the frontal sinus, and a bone thickness surrounding the frontal sinus.

The aggregator service 106 may also change an orientation of the dental image 108 based on the anatomy 222. Classification(s) may be correlated from the dental image 108 and the anatomy 222 by identifying teeth in the dental image 108; identifying a position for each of the teeth as adult or primary based on one or more of a universal number system, a palmer notation, or an international standards organization (ISO) system; identifying a maxillary, a mandible molar, and/or a canine relationship between the teeth based on an angle's classification of malocclusion; inserting the classification(s) into a patient dataset 220 in relation to the dental image 108.

In another example scenario, the aggregator service 106 may match and identify the dental image 108 with a ML pathology and treatment dataset 218. The ML pathology and treatment dataset 218 may include pathology annotation(s) and treatment annotation(s) designated to model dental image(s) associated with a dental field including endodontics, periodontics, orthodontics, prosthodontics, oral surgery, oral pathology, pediatrics, temporal mandibular joint dentistry, and/or radiology, among others in relation to the ML anatomy dataset 216. A pathology 224 and a treatment 226 from the ML pathology and treatment dataset 218 may be matched to the dental image 108.

The aggregator service 106 may match and identify the dental image 108 with the ML pathology and treatment dataset 218 using a comparative pixel value and pixel density analysis or other mechanism(s). The aggregator service 106 may learn to recognize, label and classify the pathology 224 and the treatment 226 on the dental image 108. The aggregator service 106 may compare difference(s) between the dental image 108 and the ML pathology and treatment dataset 218. The aggregator service 106 may recognize, label, and/or classify the pathology 224 and the treatment 226. The pathology 224 and the treatment 226 may be merged into the ML pathology and treatment dataset 218 in a relation to the dental image 108 for future analysis.

The ML pathology and treatment dataset 218 may include a pen-apical pathology, a widened periodontal ligament, an internal root resorption, a carious exposure of a tooth nerve, an apexification, an apicogenosis, a fractured root, a root resorption, an open apices, a short filled root canal, and/or an over extended root canal, among others as the pathology 224 within the endodontics field. The ML pathology and treatment dataset 218 may include a pulp capping, a pulpotomy, a pulpectomy, an existing root canal, a working length, a silver point root canal, and/or a apicoectomy (such as an amalgam or a mineral trioxide aggregate), among others as the treatment 226 within the endodontics field.

The ML pathology and treatment dataset 218 may include a poor crown to root ratio, a calculus, an osseous (bone) defect, a maxillary and mandible alveolar ridge resorption, a bony wall defect (such as one, two, or three type), and/or a furcation and juvenile periodontitis, among others as the pathology 224 in the periodontics field. The ML pathology and treatment dataset 218 may include an endosteal dental implant, a blade dental implant, a surgical screw, a dental implant, a mesh membrane, a resorbable membrane, non-resorbable membranes, a polytetrafluoroethylene membrane, a surgical plate, a metal suture, and/or a staple, among others as the treatment 226 within the periodontics field.

The ML pathology and treatment dataset 218 may include an anterior crowding, a posterior crowding, a diastomer, an angel's classification of malocclusion, an ankylosis, an extrusion, a cross bite, an open bite, an over jet, and/or an over bite, among others as the pathology 224 within the orthodontics field. The ML pathology and treatment dataset 218 may include a maxillary permanent retainer wire, a mandibular permanent retainer wire, an orthodontic bracket, an orthodontic distal shoe, an orthodontic metal spacer, an orthodontic spring, an elastic, a screw anchor, an orthodontic separator, an inter-proximal reduction, a bonded button, and/or a composite orthodontic attachment, among others as the treatment 226 within the orthodontics field.

The ML pathology and treatment dataset 218 may include a missing tooth, an occlusal caries, a inter-proximal caries (such as mesial or distal), a carious exposure, an incipient carious lesion, a buccal, facial, or lingual caries, an open margin around a crown, an amalgam filling, a composite filling, a fractured crown, a decay associated with a crown, a fractured cast (such as a laboratory processed) and a prefabricated post, a fractured amalgam and a composite filling, a caries under an amalgam and a composite filling, fractured onlays and inlays, a decay under onlays and inlays, an open margin around a bridge, and/or a decay associated with a bridge among others as the pathology 224 within the prosthodontics field. The ML pathology and treatment dataset 218 may include a crown, a bridge, a laboratory cast post, a prefabricated post, inlays and onlays, an amalgam filling, a composite filling, a core build up, an implant abutment, a screw retained implant crown, a cementable implant crown, an integrated abutment crown (IAC) and/or an implant healing abutment, among others as the treatment 226 within the prosthodontics field.

The ML pathology and treatment dataset 218 may include a third molar impaction (such as a soft tissue impaction, a partial bony impaction, a full bony impaction, or a horizontal), an aberrant tooth positioning (such as a retained adult and baby tooth), a mesial and distal drifting of a tooth, a fractured (retained) root tip, a failed apicoectomy, a fractured root, a cleft palate, a fractured natural crown, a caries on a root of a tooth, a temporomandibular joint (TMJ), a size of the TMJ disk, a degenerative process on the TMJ, a foreign body in a sinus, and/or a dental implant in the maxillary sinus, among others as the pathology 224 within the oral surgery field. The ML pathology and treatment dataset 218 may include a apicoectomy, a surgical plate, a surgical wire, and/or a surgical screw, among others as the treatment 226 within the oral surgery field.

The ML pathology and treatment dataset 218 may include a radicular cyst, a dental granuloma, a dentigerous cyst, an incisive canal cyst, an odontogenenic myxoma, a keratocyst, a sialolith, an ameloblastoma, an odontoma, a torus, an osteoma, an osteochondroma, a cementoblastoma, an osteogenic sarcoma, a pagets disease, a fibrous dysplasia, a fibro-sarcoma, a hemangioma, a lymphoma, a giant cell tumor, an aneurysmal bone cyst, a meningioma, a ewing sarcoma, a hyperparathyroidism, a bisphosphonate osteo necrosis, an ossifying fibroma, a cemento osseous dysplasia, an osteosarcoma, and/or a metastasis, among others as the pathology 224 within the oral pathology field.

The ML pathology and treatment dataset 218 may include an amylogenesis imperfect, an enamel hypoplasia, a hyper-fluorosis, a hypo-fluorosis, an open apices, a traumatic intrusion, an ankylosis, and/or a caries index, among others as the pathology 224 within the pediatric dentistry field. The ML pathology and treatment dataset 218 may include an identification of a dental age, a leeway space, a genetically missing permanent tooth, an apicogenesis, a stainless steel prefabricated crown, a fixed space maintainer, a unilateral and bilateral distal shoe, and/or a palatal expansion device, among others as the treatment 226 within the pediatric dentistry field.

The ML pathology and treatment dataset 218 may include an arthritis, a collapsed disc, an anterior disc displacement with a reduction, an anterior disc displacement without a reduction, a chipped or thinned incisal edge, and/or an abfraction flattened occlusal plane, among others as the pathology 224 within the TMJ dentistry field.

The aggregator service 106 may also perform additional ML operation(s) on the dental image 108 to identify attributes and annotate the dental image 108. The additional ML operation(s) may include identifying the left and right temporomandibular joints (TMJ) and measuring the TMJ space. The additional ML operations(s) may also include identifying x-ray error(s). The x-ray error(s) may include a cone cut, a failure to completely close on a bitewing tab, a fore shorting, a fore longing, a double exposure, an overlap, a no exposure, an over exposure, overlapping images, a periapical (PA) without imaging root apex, an incomplete imaging, reversed images (left/right) and (top/bottom), and/or a counter-clock wise image, among others. Furthermore, the additional ML operation(s) may include identifying an earring, a nose ring, a tongue ring, eyeglasses, and/or piercings and jewelry, among others.

Figure 3:
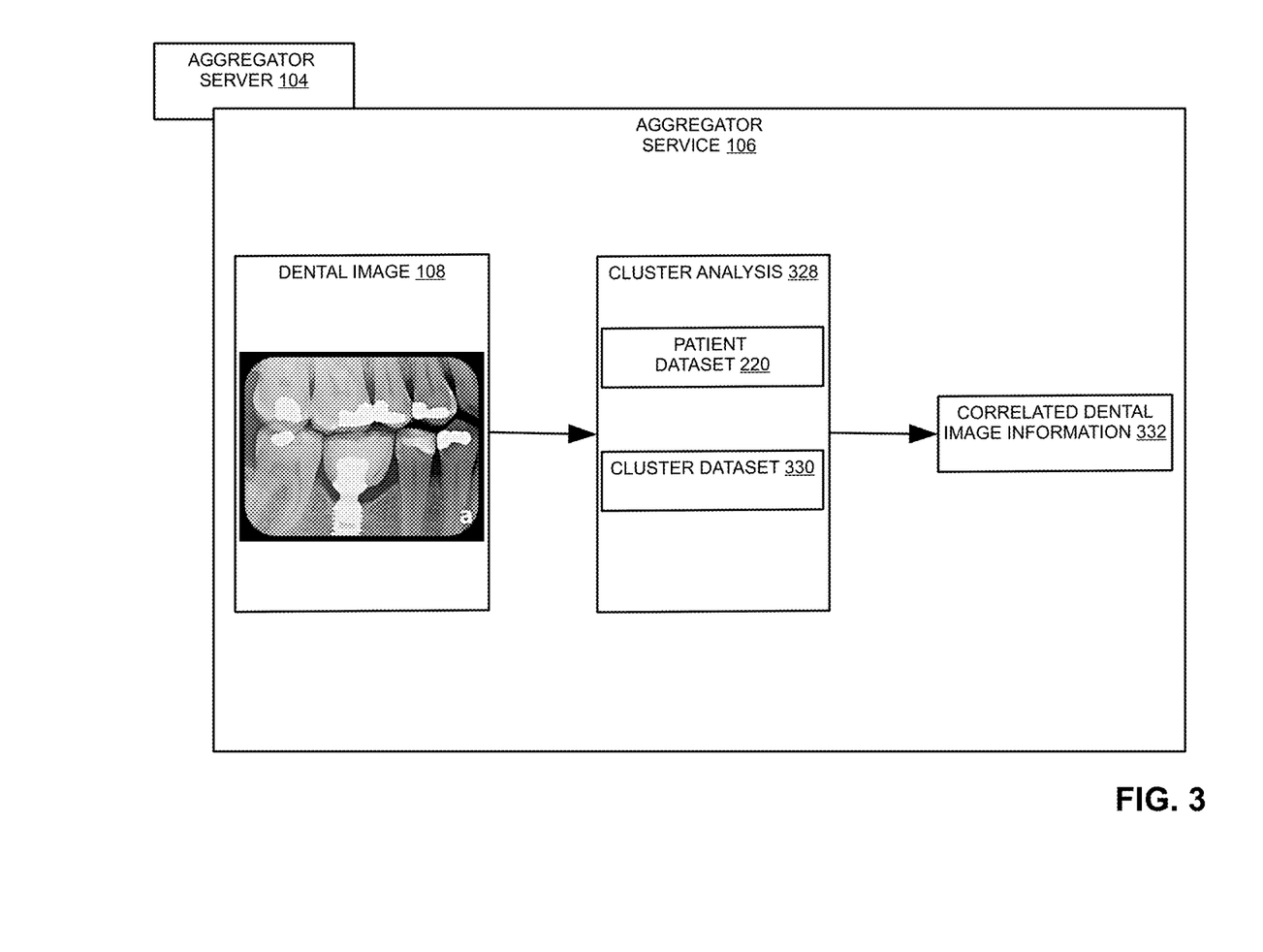
FIG. 3 shows a display diagram illustrating a cluster analysis to produce a correlated dental image information, according to an embodiment of the invention.

FIG. 3 shows a display diagram illustrating a cluster analysis to produce a correlated dental image information 332. The aggregator service 106 (executed by the aggregator server 104) may query and receive the patient dataset 220 of the patient associated with the dental image 108 from a patient data provider. The patient data provider may include a records management entity that hosts and manages data/information associated with a number of patients. The patient dataset 220 may include patient information such as an age, a first name, a gender, a middle initial, a last name, a date of birth, a zip code, an address, a cell phone number, a land line number, a current medication, a previous medication, a social security number, a material status, an insurance, a patient's insurance identification number, a patient's email address, a change of insurance, a change of employment, a change of zip code, a change of the previous medication, a change of the marital status, and/or a change of the gender, among others associated with the patient.

The dental image 108, capture information associated with the dental image 108 (such as a time, a location, and/or a source, among others) and the anatomy 222, the pathology 224, and/or the treatment 226 associated with the dental image 108 may be inserted to the patient dataset 220. The aggregator service 106 may also identify whether the patient is informed in regards to a notification obligation such as a health insurance portability and accountability act (HIPAA), an end user licensing agreement (EULA), a system and method licensing agreement (SLA), a security token, a swipe authorization, and/or signed consent form by analyzing the patient dataset 220 for attributes associated with the notification obligation.

Furthermore, the aggregator service 106 may compare difference(s) between the dental image 108 (and associated annotations) and the attributes of the patient dataset 220. The aggregator service 106 may recognize, label, and/or classify the dental image 108 (and the associated annotations) based on the patient dataset 220 (and/or attributes).

A cluster analysis 328 of the dental image 108 and/or the patient dataset 220 may be performed with a cluster dataset 330 to produce the correlated dental image information 332. The cluster dataset 330 may include annotated information associated with a population and dental classifications associated with the population. The cluster analysis 328 may compare attributes of the patient dataset 220 (such as the patient information, the capture information, the anatomy 222, the pathology 224, and/or the treatment 226) to elements of the cluster dataset 330. As such, the correlated dental image information 332 may include attributes of the patient dataset 220 (such as the dental image 108 and the annotations) that are further annotated with elements of the cluster dataset 330.

Furthermore, the cluster analysis 328 may be performed based on a spatial detection, a sequential pattern mining, dataset(s) comparison, a data analysis, a statistical data analysis, a Boolean Logic analysis, a fuzzy logic analysis, an ML analysis, and/or an anomaly detection analysis mechanism, among others. In addition, the correlated dental image information 332 may be merged into the cluster dataset 330 to present a future cluster analysis with an expanded version of the cluster dataset 330.

In addition, the aggregator service 106 may compare difference(s) between the dental image 108 (and associated annotations) and the elements of the cluster dataset 330. The aggregator service 106 may recognize, label, and/or classify the dental image 108 (and the associated annotations) based on the element(s) the cluster dataset 330 (and/or attributes).

Figure 4:
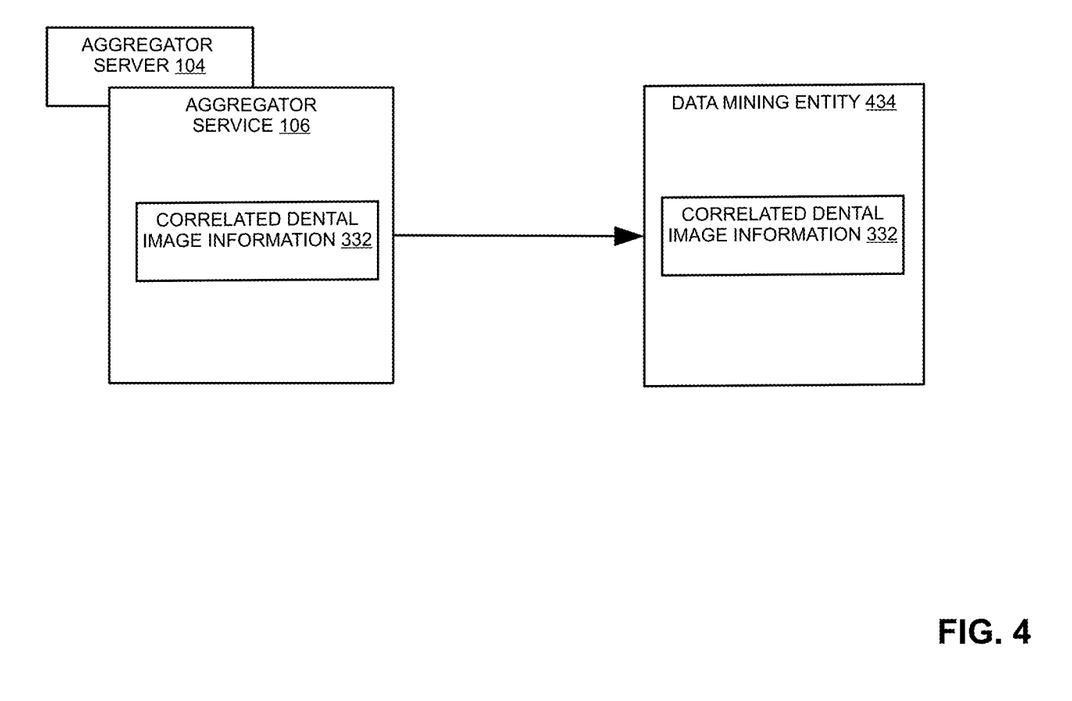
FIG. 4 shows a display diagram illustrating a transmission of the correlated dental image information to a data mining entity, according to an embodiment of the invention.

FIG. 4 shows a display diagram illustrating a transmission of the correlated dental image information 332 to a data mining entity 434. In an example scenario, the data mining entity 434 may include an insurance data mining service. The insurance data mining service may be provided by a dental insurance and/or a medical insurance organization. The aggregator service 106 may generate the correlated dental image information 322 by analyzing the patient dataset 220 (which includes the dental image 108 and the annotations) with an insurance dataset. As such, the correlated dental image information 332 may include attributes of the patient dataset 220 (such as the dental image 108 and the annotations) that are further annotated with elements of the insurance dataset. The aggregator service 106 may also format the correlated dental image information 332 as an insurance claim. In addition, the aggregator service 108 may integrate the correlated dental image information 332 to a new or an existing insurance claim. The correlated dental image information 338 may also be analyzed and merged (or integrated) into the insurance dataset to expand the insurance dataset for a future analysis.

The aggregator service 106 may also identify whether the patient is informed in regards to a notification obligation such as a health insurance portability and accountability act (HIPAA), an EULA, a SLA, a security token, a swipe authorization, and/or signed consent form by analyzing the correlated dental image information 338 (annotated with the insurance dataset) for attributes associated with the notification obligation.

The aggregator service 106 may also identify discrepancy(s) between dental insurance claim(s) by analyzing and comparing attributes of the correlated dental image information 338 with elements of the insurance dataset including American dental association (ADA) code(s), a date, a claim identifier, a claim number, multiple or duplicate claims (instead of a single claim), a national provider identification number for provider/institution(s) associated with the patient, and/or a provider's state license number, among others. Corrective action to merge the discrepancy(s) may be implemented automatically to remove the discrepancy(s) between the correlated dental image information 338, the patient dataset 220, and/or the insurance claim(s) from the insurance dataset. Alternatively, corrective action may be implemented manually based on feedback and/or input from a user associated with the aggregator service 106 regarding the discrepancy(s).

In another example scenario, the data mining entity 434 may include a bioinformatics data mining service. The bioinformatics data mining service may be provided by a bioinformatics organization (such as a research organization). The aggregator service 106 may generate the correlated dental image information 322 by analyzing the patient dataset 220 (which includes the dental image 108 and the annotations) with an bioinformatics dataset. As such, the correlated dental image information 332 may include attributes of the patient dataset 220 (such as the dental image 108 and the annotations) that are further annotated with elements of the bioinformatics dataset. The correlated dental image information 338 may also be merged into the bioinformatics dataset to expand the bioinformatics dataset for a future analysis.

The aggregator service 106 may also identify whether the patient is informed in regards to a notification obligation such as a HIPAA, an EULA, a SLA, a security token, a swipe authorization, and/or signed consent form by analyzing the correlated dental image information 338 (annotated with the insurance dataset) for attributes associated with the notification obligation.

The aggregator service 106 may also identify matching elements of the bioinformatics dataset including gene(s), gene identifier, a gene sequence, single nucleotide polymorphism(s), nucleic acid sequence(s), protein sequence(s) (proteomics), annotating genome(s), a shotgun sequence, an associated periodontal disease, a caries susceptibility, an impacted tooth, a tooth loss, an angle's classification of malocclusion, level(s) of immunoglobulin G (IGG) and immunoglobulin A (IGA), and/or diabetes diagnosis, among others by matching the attributes of the correlated dental image information 338 with elements of the bioinformatics dataset. The attributes of the correlated dental image information 338 may further be annotated with the elements matched from the bioinformatics dataset.

In another example scenario, the aggregator service 106 may verify an authorization by the patient to allow an analysis of the dental image. In response to a determination that the patient authorized the analysis of the dental image, the aggregator service 106 may continue with processing the dental image with the ML anatomy dataset. In response to a failure to verify the authorization by the patient, the aggregator service 106 may stop operations associated with the dental image.

In yet another example scenario, the aggregator service 106 may verify a compliance of the dental image and/or the correlated dental image information 338 with a regulatory policy. An example of the regulatory policy may include a HIPAA regulation. In response to a determination that the dental image and/or the correlated dental image information 228 may be compliant with the regulatory policy, the aggregator service 106 may provide the correlated dental image information 338 and/or the dental image to the data mining entity for further processing and to compile the diagnostic aid for a user. Alternatively, if the dental image and/or the correlated dental image information 338 may be determined as not in a compliance of the regulatory policy then the dental image and/or the correlated dental image information 338 may not be provided to the data mining entity for further processing.

The example scenarios and schemas in FIGS. 1 through 4 are shown with specific components, data types, and configurations. Embodiments are not limited to systems according to these example configurations. Data mining of a dental image may be implemented in configurations employing fewer or additional components in applications and user interfaces. Furthermore, the example schema and components shown in FIGS. 1 through 4 and their subcomponents may be implemented in a similar manner with other values using the principles described herein.

Figure 5:
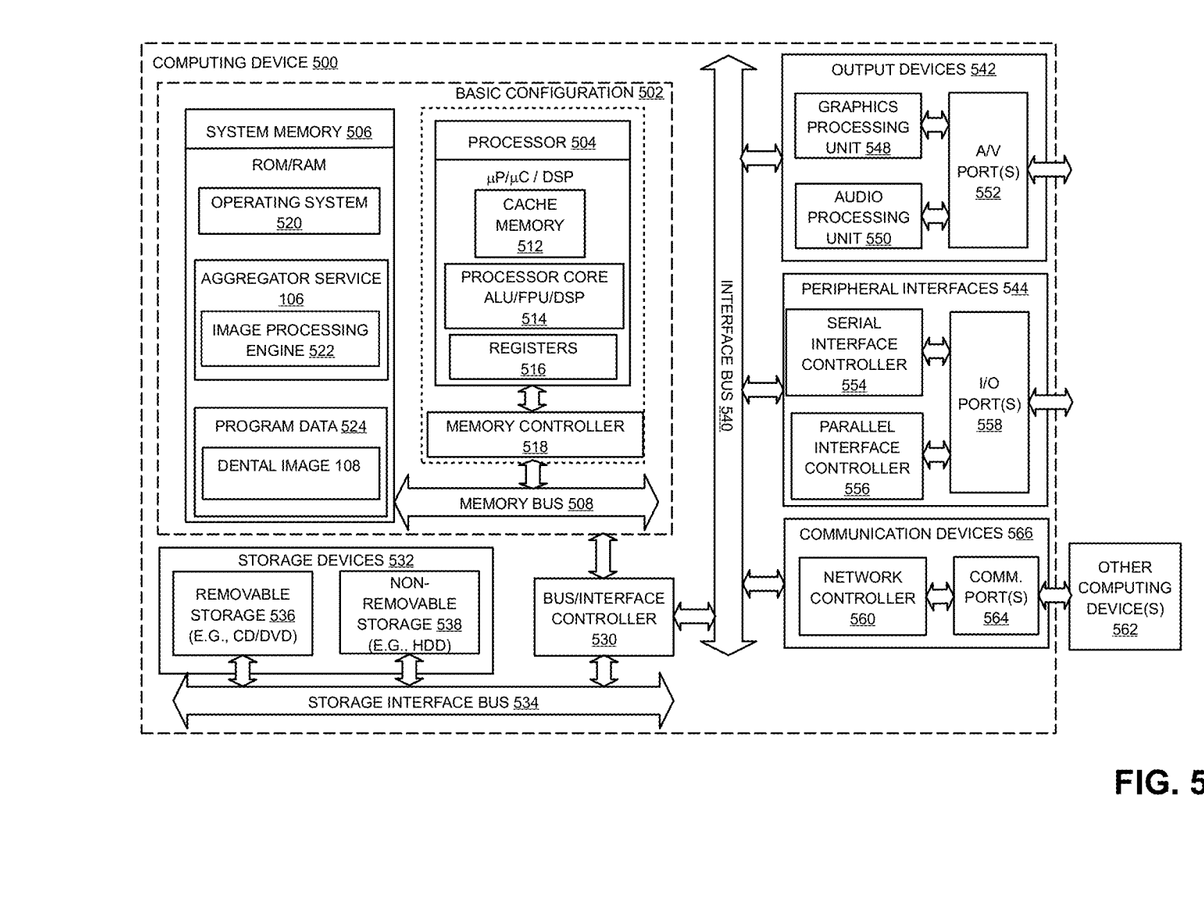
FIG. 5 is a block diagram of an example computing device, which may be used to provide data mining of a dental image.

FIG. 5 is a block diagram of an example computing device, which may be used to provide data mining of a dental image, according to embodiments.

For example, computing device 500 may be used as a server, desktop computer, portable computer, smart phone, special purpose computer, or similar device. In a basic configuration 502, the computing device 500 may include one or more processors 504 and a system memory 506. A memory bus 508 may be used for communication between the processor 504 and the system memory 506. The basic configuration 502 may be illustrated in FIG. 5 by those components within the inner dashed line.

Depending on the desired configuration, the processor 504 may be of any type, including but not limited to a microprocessor (μP), a microcontroller (μC), a digital signal processor (DSP), or any combination thereof. The processor 504 may include one more levels of caching, such as a level cache memory 512, one or more processor cores 514, and registers 516. The example processor cores 514 may (each) include an arithmetic logic unit (ALU), a floating-point unit (FPU), a digital signal processing core (DSP Core), a graphics processing unit (GPU), or any combination thereof. An example memory controller 518 may also be used with the processor 504, or in some implementations, the memory controller 518 may be an internal part of the processor 504.

Depending on the desired configuration, the system memory 506 may be of any type including but not limited to volatile memory (such as RAM), non-volatile memory (such as ROM, flash memory, etc.), or any combination thereof. The system memory 506 may store and provide an operating system 520, an aggregator service 106, and a program data 524. The aggregator service 106 may include components such as an image processing engine 522. The image processing engine 522 may execute the instructions and processes associated with the aggregator service 106. In an example scenario, the image processing engine 522 may receive a dental image of a patient from a dental image provider. Next, the dental image may be processed with a ML anatomy dataset. An anatomy from the ML anatomy dataset may be identified and matched to the dental image. The dental image may also be matched and identified with a ML pathology and treatment dataset. A pathology and a treatment from the ML pathology and treatment dataset may be matched to the dental image. Subsequently, the dental image and the anatomy, the pathology, and the treatment associated with the dental image may be inserted to a patient dataset associated with the patient. In addition, a cluster analysis of the patient dataset may be performed with a cluster dataset to produce a correlated dental image information. Furthermore, the correlated dental image information may be provided to a data mining entity and to compile a diagnostic aid for a user.

Input to and output out of the aggregator service 106 may be transmitted through a communication device 566 that may be communicatively coupled to the computing device 500. The communication device 566 may provide wired and/or wireless communication. The program data 524 may also include, among other data, the dental image 108, or the like, as described herein. The dental image 108 may include an x-ray image and/or a photographic image of dental structure(s) of the patient.

The computing device 500 may have additional features or functionality, and additional interfaces to facilitate communications between the basic configuration 502 and any desired devices and interfaces. For example, a bus/interface controller 530 may be used to facilitate communications between the basic configuration 502 and one or more data storage devices 532 via a storage interface bus 534. The data storage devices 532 may be one or more removable storage devices 536, one or more non-removable storage devices 538, or a combination thereof. Examples of the removable storage and the non-removable storage devices may include magnetic disk devices, such as flexible disk drives and hard-disk drives (HDDs), optical disk drives such as compact disk (CD) drives or digital versatile disk (DVD) drives, solid state drives (SSDs), tape drives, flash memory, cloud based storage, a cloud computing platform providing a storage service, an open or a closed source platform providing a storage service, a virtual private network (VPN) providing a storage service, an ISO image disk, a cloud based storage service, a redundant array of independent disks (RAID), a USB based disk drive, a USB flash drive, a storage virtualization based storage service, a digital video service, a virtualized server providing a storage service, a super computer providing a storage service, a super computer parallel array providing a storage service, a dental practice management software providing a storage service, a dental digital x-ray software providing a storage service, and/or all future embodiments. Example computer storage media may include volatile and nonvolatile, removable, and non-removable media implemented in any method or technology for storage of information, such as computer-readable instructions, data structures, program modules, all future embodiments, or other data.

The system memory 506, the removable storage devices 536 and the non-removable storage devices 538 are examples of computer storage media. Computer storage media includes, but is not limited to, RAM, ROM, EEPROM, flash memory or other memory technology, CD-ROM, digital versatile disks (DVDs), solid state drives, or other optical storage, magnetic cassettes, magnetic tape, magnetic disk storage or other magnetic storage devices, or any other medium which may be used to store the desired information and which may be accessed by the computing device 500. Any such computer storage media may be part of the computing device 500.

The computing device 500 may also include an interface bus 540 for facilitating communication from various interface devices (for example, one or more output devices 542, one or more peripheral interfaces 544, and one or more communication devices 566) to the basic configuration 502 via the bus/interface controller 530. Some of the example output devices 542 include a graphics processing unit 548 and an audio processing unit 550, which may be configured to communicate to various external devices such as a display or speakers via one or more A/V ports 552. One or more example peripheral interfaces 544 may include a serial interface controller 554 or a parallel interface controller 556, which may be configured to communicate with external devices such as input devices (for example, keyboard, mouse, pen, voice input device, touch input device, etc.) or other peripheral devices (for example, printer, scanner, etc.) via one or more I/O ports 558. An example of the communication device(s) 566 includes a network controller 560, which may be arranged to facilitate communications with one or more other computing devices 562 over a network communication link via one or more communication ports 564. The one or more other computing devices 562 may include servers, computing devices, and comparable devices.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

The computing device 500 may be implemented as a part of a specialized server, mainframe, or similar computer, which includes any of the above functions. The computing device 500 may also be implemented as a personal computer including both laptop computer and non-laptop computer configurations. Additionally, the computing device 500 may include specialized hardware such as an application-specific integrated circuit (ASIC), a field programmable gate array (FPGA), a programmable logic device (PLD), and/or a free form logic on an integrated circuit (IC), among others.

Example embodiments may also include methods to provide data mining of a dental image. These methods can be implemented in any number of ways, including the structures described herein. One such way may be by machine operations, of devices of the type described in the present disclosure. Another optional way may be for one or more of the individual operations of the methods to be performed in conjunction with one or more human operators performing some of the operations while other operations may be performed by machines. These human operators need not be collocated with each other, but each can be only with a machine that performs a portion of the program. In other embodiments, the human interaction can be automated such as by pre-selected criteria that may be machine automated.

Figure 6:
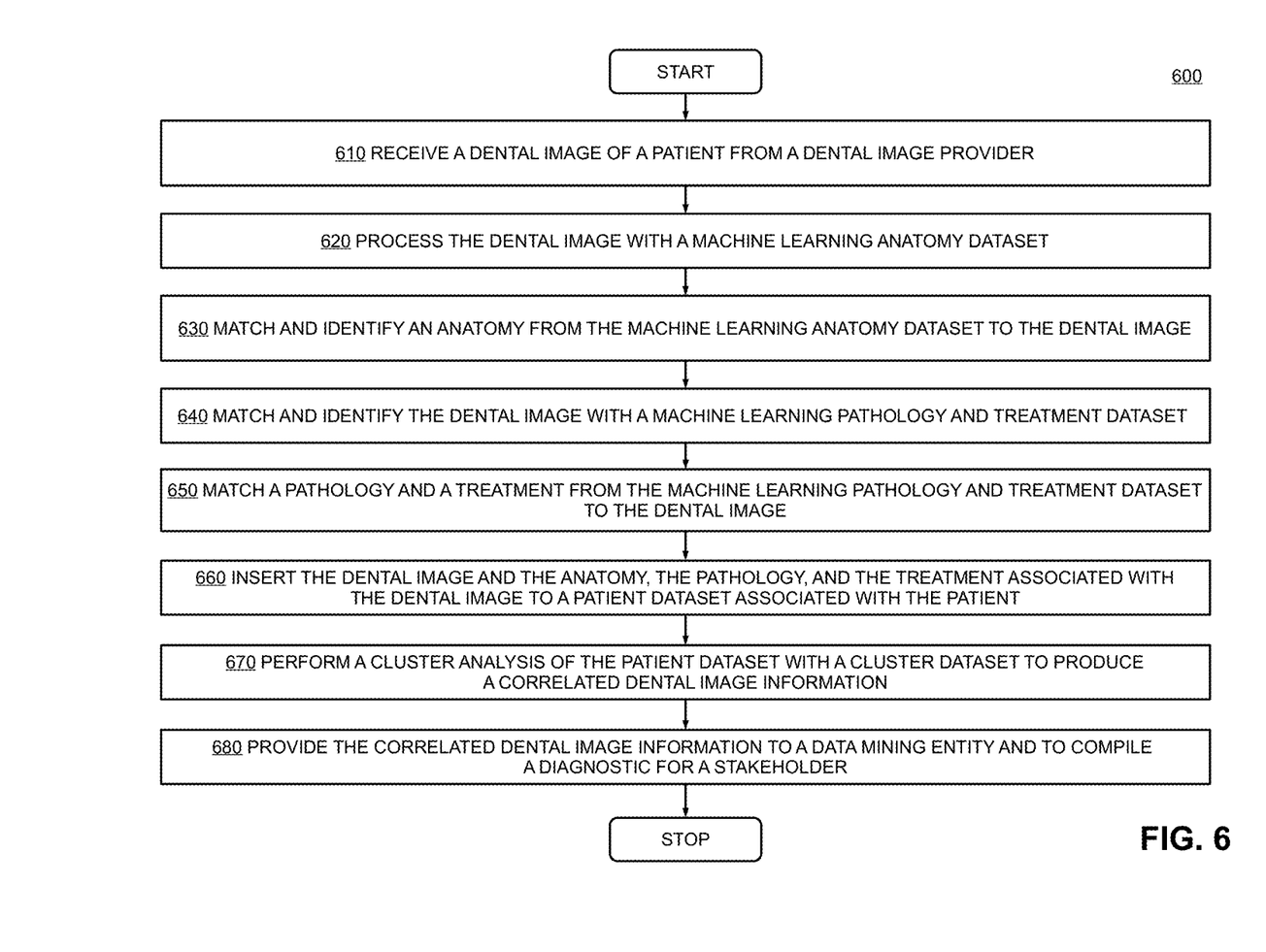
FIG. 6 is a logic flow diagram illustrating a process for providing data mining of a dental image, according to an embodiment of the invention.

FIG. 6 is a logic flow diagram illustrating a process for providing data mining of a dental image. Process 600 may be implemented on a computing device, such as the computing device 500 or another system.

Process 600 begins with operation 610, where an aggregator service may receive a dental image of a patient from a dental image provider. Next, at operation 620, the dental image may be processed with a ML anatomy dataset. At operation 630, an anatomy from the ML anatomy dataset may be identified and matched to the dental image. At operation 640, the dental image may also be matched and identified with a ML pathology and treatment dataset. At operation 650, a pathology and a treatment from the ML pathology and treatment dataset may be matched to the dental image.

Subsequently, at operation 660, the dental image and the anatomy, the pathology, and the treatment associated with the dental image may be inserted to a patient dataset associated with the patient. In addition, at operation 670, a cluster analysis of the patient dataset may be performed with a cluster dataset to produce a correlated dental image information. Furthermore, at operation 680, the correlated dental image information may be provided to a data mining entity and to compile a diagnostic aid for a user.

The operations included in process 600 is for illustration purposes. Data mining of a dental image may be implemented by similar processes with fewer or additional steps, as well as in different order of operations using the principles described herein. The operations described herein may be executed by one or more processors operated on one or more computing devices, one or more processor cores, specialized processing devices, and/or special purpose processors, among other examples.

A method of providing data mining of a dental image is also described. The method may include receiving a dental image of a patient from a dental image provider. The dental image may next be processed with a ML anatomy dataset. An anatomy from the ML anatomy dataset may be identified and matched to the dental image. The dental image may also be matched and identified with a ML pathology and treatment dataset. A pathology and a treatment from the machine leaning pathology and treatment dataset may be matched to the dental image. In addition, a patient dataset of the patient associated with the dental image may be queried and received from a patient data provider. Subsequently, the dental image and the anatomy, the pathology, and the treatment associated with the dental image may be inserted to the patient dataset. Furthermore, a cluster analysis of the patient dataset may be performed with a cluster dataset to produce a correlated dental image information. Moreover, the correlated dental image information may be provided to a data mining entity and to compile a diagnostic aid for a user.

When introducing elements of the present disclosure or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A system for providing data mining of a dental image, the system comprising:
    an aggregator server, wherein the aggregator server is configured to:

receive a dental image of a patient from a dental image provider, wherein the dental image provider is an e-commerce service;

process the dental image with a machine learning (ML) anatomy dataset;

match and identify an anatomy from the ML anatomy dataset to the dental image;

match and identify the dental image with a ML pathology and treatment dataset;

match a pathology and a treatment from the machine leaning pathology and treatment dataset to the dental image;

insert the dental image and the anatomy, the pathology, and the treatment associated with the dental image to a patient dataset associated with the patient;

perform a cluster analysis of the patient dataset with a cluster dataset to produce a correlated dental image information;

provide the correlated dental image information to a data mining entity and to compile a diagnostic aid for a user;

format the correlated dental image information based on another dataset associated with the data mining entity;

merge the correlated dental image information into the data mining entity dataset; and identify and correct a discrepancy between the correlated dental image information and the data mining entity dataset.

2. The aggregator server of claim 1, wherein the dental image is obtained from one or more of: a digital image, a film based x-ray, a digitally scanned x-ray, a digitally captured x-ray, a scintillator technology based image, a trans-illumination image, a florescence technology based image, a blue florescence technology based image, a laser based technology based image, and a computed tomography (CT) scan based image.

3. The aggregator server of claim 1, wherein the dental image provider utilizes an image capture device or a data storage device.

4. The aggregator server of claim 3, wherein the capture image device includes one or more of: an x-ray equipment, a scintillator counter, an indirect or direct flat panel detector (FPD), a charged couple device (CCD), a phosphor plate radiography device, a picture archiving and communication system (PACS), a photo-stimulable phosphor (PSP) device, a computer tomography (CT) device, a wireless complementary metal-oxide-semiconductor (CMOS), a cone beam computed tomography (CBCT) device.

5. The aggregator server of claim 1, wherein the aggregator server is further configured to:
change an orientation of the dental image based on the anatomy;
correlate one or more classifications from the dental image and the anatomy with at least one operation to:
identify teeth in the dental image;
identify a position for each of the teeth as adult or primary based on one or more of a universal number system, a palmer notation, or an international standards organization (ISO) system;
identify one or more of a maxillary, a mandible molar, or a canine relationship between the teeth based on an angle's classification of malocclusion; and
insert the one or more classifications into the patient dataset in relation to the dental image.

6. The aggregator server of claim 1, wherein the aggregator server is further configured to:

determine the anatomy associated with the dental image by performing at least one operation to:
differentiate the dental image as a left or a right vertical bite wing image;
differentiate the dental image as a left or a right horizontal bite wing image;
differentiate the dental image as a left or a right maxillary periapical image;
differentiate the dental image as a left or a right mandibular periapical image;
differentiate the dental image as a maxillary or mandibular anterior image;
differentiate the dental image as a left or a right side of a panoramic image;
differentiate the dental image as including an absent tooth or a present tooth; or
differentiate the dental image as including a cephalometric image with an over bite, an over jet, an angle's classification of malocclusion, an airway space or a sleep apnea.

7. The aggregator server of claim 1, wherein the aggregator server is further configured to:
determine the anatomy associated with the dental image by performing at least one operation to:
differentiate the dental image as a maxillary image or a mandible image;
differentiate the dental image as a left or a right temporal mandibular joint image;
identify and measure one or more of: a mandibular canal, an inferior alveolar nerve space, a mental foramen, a staphne's cyst, a mandible foramen, a condylar process, a mandibular coronoid process, a sublingual fossa, a ramus, a alveolar crest, a mental protuberance, a mental tubercle, a mylohyoid grove, a mylohyoid line, a lingual, a pterygoid fossa, an incisive canal, a zygomatic bone, a maxillary sinus, a curve of spee, a diastomer, a tooth bud, a germination, a fused teeth, a full or partial septum, an open bite, a cross bite, an over jet, or an over bite associated with the dental image;
identify and measure one or more of a maxillary sinus size and volume, a bone thickness of a floor of a maxillary sinus, a bone thickness surrounding the maxillary sinus, a graft placed in the maxillary sinus, and a septum in the maxillary sinus;
identify a post-surgical maxillary sinus or mandibular alveolar ridge splitting procedure; and
identify a frontal sinus, a graft placed in the frontal sinus, and a bone thickness surrounding the frontal sinus.

8. The aggregator server of claim 1, wherein the pathology and the treatment dataset includes one or more pathology annotations and one or more treatment annotations designated to one or more model dental images associated with a dental field including one or more of: endodontics, periodontics, orthodontics, prosthodontics, oral surgery, oral pathology, pediatrics, temporal mandibular joint dentistry, and radiology.

9. An aggregator server for providing data mining of a dental image, the aggregator server comprising:
a computer vision component configured to analyze the dental image,
a memory configured to store instructions associated with an aggregator service,
a processor coupled to the computer vision component and the memory, the processor executing the instructions associated with the aggregator service, wherein the aggregator service includes:
an image processing engine configured to:
receive a dental image of a patient from a dental image provider, wherein the dental image provider is an e-commerce service;
process the dental image with a machine learning (ML) anatomy dataset;
match and identify an anatomy from the ML anatomy dataset to the dental image;
match and identify the dental image with a ML pathology and treatment dataset;
match a pathology and a treatment from the ML pathology and treatment dataset to the dental image;
query and receive a patient dataset of the patient associated with the dental image from a patient data provider;
insert the dental image and the anatomy, the pathology, and the treatment associated with the dental image to the patient dataset;
perform a cluster analysis of the patient dataset with a cluster dataset to produce a correlated dental image information;
provide the correlated dental image information to a data mining entity and to compile a diagnostic aid for a user;
format the correlated dental image information based on another dataset associated with the data mining entity;
merge the correlated dental image information into the data mining entity dataset; and
identify and correct a discrepancy between the correlated dental image information and the data mining entity dataset.

10. The aggregator server of claim 9, wherein the dental image is processed with the ML anatomy dataset upon a process to:
verify an authorization by the patient to analyze the dental image.

11. The aggregator server of claim 10, wherein the correlated dental image information is provided to a data mining entity upon a process to:
verify a compliance of the dental image and the correlated dental image information with a regulatory policy.

12. The aggregator server of claim 11, wherein the regulatory policy includes health insurance portability and accountability act (HIPAA).

13. The aggregator server of claim 9, wherein the dental image is not processed with the ML anatomy dataset in response to a failure to determine an authorization by the patient to analyze the dental image.

14. The aggregator server of claim 9, wherein the patient dataset includes one or more of an age, a first name, a gender, a middle initial, a last name, a date of birth, a zip code, an address, a cell phone number, a land line number, a current medication, a previous medication, a social security number, a material status, an insurance, a patient's insurance identification number, a patient's email address, a change of insurance, a change of employment, a change of zip code, a change of the previous medication, a change of the marital status, and a change of the gender associated with the patient.

15. The aggregator server of claim 9, wherein the data mining entity includes a dental insurance data mining service, and wherein the dental insurance data mining provides an insurance dataset including one or more of an American dental association (ADA) code, a date, a claim identifier, a claim number, a duplicate claim associated with the claim identifier, a national provider identification number for a provider associated with a patient, and a provider's state license number to further analyze and integrate the correlated dental image information.

16. The aggregator server of claim 9, wherein the data mining entity includes a bioinformatics data mining service, and wherein the bioinformatics data mining service provides a bioinformatics dataset including one or more of a gene identifier, a gene sequence, a single nucleotide polymorphism, a nucleic acid sequence, a protein sequence, an annotating genome, a shotgun sequence, a periodontal disease, a caries susceptibility, an impacted tooth, a tooth loss, an angle's classification of malocclusion, and a diabetes diagnosis to further analyze and integrate the correlated dental image information.

17. A method of providing data mining of a dental image, the method comprising:
receiving a dental image of a patient from a dental image provider;
processing the dental image with a machine learning (ML) anatomy dataset;
matching and identifying an anatomy from the ML anatomy dataset to the dental image;
matching and identifying the dental image with a ML pathology and treatment dataset;
matching a pathology and a treatment from the ML pathology and treatment dataset to the dental image;
querying and receive a patient dataset of the patient associated with the dental image from a patient data provider;
inserting the dental image and the anatomy, the pathology, and the treatment associated with the dental image to the patient dataset;
performing a cluster analysis of the patient dataset with a cluster dataset to produce a correlated dental image information;
providing the correlated dental image information to a data mining entity and to compile a diagnostic aid for a user;
formatting the correlated dental image information based on another dataset associated with the data mining entity;
merging the correlated dental image information into the data mining entity dataset; and
identifying and correcting a discrepancy between the correlated dental image information and the data mining entity dataset.

* * * * *